(12) United States Patent
Choate

(10) Patent No.: US 7,985,577 B2
(45) Date of Patent: *Jul. 26, 2011

(54) SYSTEMS AND PROCESSES FOR TREATMENT OF ORGANIC WASTE MATERIALS WITH A BIOMIXER

(75) Inventor: Chris E. Choate, San Francisco, CA (US)

(73) Assignee: Recology, Inc., San Francisco, CA (US)

( * ) Notice: Subject to any disclaimer, the term of this patent is extended or adjusted under 35 U.S.C. 154(b) by 1082 days.

This patent is subject to a terminal disclaimer.

(21) Appl. No.: 11/492,258

(22) Filed: Jul. 24, 2006

(65) Prior Publication Data

US 2007/0231877 A1   Oct. 4, 2007

Related U.S. Application Data

(63) Continuation-in-part of application No. 11/385,098, filed on Mar. 20, 2006, which is a continuation-in-part of application No. 10/427,454, filed on Apr. 30, 2003, now Pat. No. 7,015,028.

(60) Provisional application No. 60/749,352, filed on Dec. 9, 2005.

(51) Int. Cl.
| | |
|---|---|
| C12M 1/00 | (2006.01) |
| C12M 3/00 | (2006.01) |
| C02F 3/34 | (2006.01) |
| C12N 1/00 | (2006.01) |
| C12N 1/12 | (2006.01) |
| C12N 1/20 | (2006.01) |
| C12P 1/00 | (2006.01) |

(52) U.S. Cl. ....... 435/267; 435/41; 435/243; 435/252.1; 435/262; 435/298.2; 435/801; 435/821; 435/822

(58) Field of Classification Search .......................... None
See application file for complete search history.

(56) References Cited

U.S. PATENT DOCUMENTS

| | | | |
|---|---|---|---|
| 1,617,014 A | 2/1927 | Derleth |
| 1,713,507 A | 5/1929 | Ammon |
| 1,752,290 A | 4/1930 | Ammon |
| 1,818,570 A | 8/1931 | Mursch |
| 1,871,489 A | 8/1932 | Ammon |
| 1,938,500 A | 12/1933 | Schur |
| 1,938,647 A | 12/1933 | Earp-Thomas |
| 2,121,371 A | 6/1938 | Traylor |
| 2,317,992 A | 5/1943 | Grether |
| 2,333,246 A | 11/1943 | Harris |
| 2,333,247 A | 11/1943 | Harris et al. |
| 2,344,591 A | 3/1944 | Bried |
| 2,344,611 A | 3/1944 | Harris |
| 2,723,954 A | 11/1955 | Young |
| 2,823,106 A | 2/1958 | Pierson |
| 2,969,277 A | 1/1961 | Carlsson et al. |
| 3,055,744 A | 9/1962 | Petersen |
| 3,236,604 A | 2/1966 | Pierson |
| 3,325,369 A | 6/1967 | Somerville |
| 3,365,395 A | 1/1968 | McDonald |
| 3,653,871 A | 4/1972 | Tempe |
| 3,734,988 A | 5/1973 | Aintablian |
| 3,814,588 A | 6/1974 | Eweson et al. |
| 3,848,813 A | 11/1974 | Stanczyk et al. |
| 3,897,215 A | 7/1975 | Davidson, Jr. et al. |
| 3,930,799 A | 1/1976 | Eweson |
| 3,932,166 A | 1/1976 | Vignovich et al. |
| 3,970,546 A | 7/1976 | Webb et al. |
| 3,984,484 A | 10/1976 | Scremin et al. |
| 4,010,098 A | 3/1977 | Fassell |
| 4,079,837 A | 3/1978 | Grube et al. |
| 4,093,516 A | 6/1978 | Lang |
| 4,094,740 A | 6/1978 | Lang |
| 4,134,731 A | 1/1979 | Houser |
| 4,203,755 A | 5/1980 | Ruckstuhl |
| 4,264,352 A | 4/1981 | Houser |
| 4,321,150 A | 3/1982 | McMullen |
| 4,326,874 A | 4/1982 | Burklin |
| 4,342,830 A | 8/1982 | Holloway |
| 4,361,239 A | 11/1982 | Kumandan |
| 4,448,588 A | 5/1984 | Cheng |
| 4,483,704 A | 11/1984 | Easter, II |
| 4,540,495 A | 9/1985 | Holloway |
| 4,632,692 A | 12/1986 | Lebesgue et al. |
| 4,769,149 A | 9/1988 | Nobilet et al. |
| 4,844,351 A | 7/1989 | Holloway |
| 4,846,975 A | 7/1989 | Kelyman |

(Continued)

FOREIGN PATENT DOCUMENTS

CA    2335140 A1    1/2000

(Continued)

OTHER PUBLICATIONS

Biomass Test Burn Report of the Tampa Electric Company, Apr. 2002, 13 pages.

(Continued)

*Primary Examiner* — Debbie K Ware
(74) *Attorney, Agent, or Firm* — Gard & Kaslow LLP

(57) ABSTRACT

Waste material is screened to produce unders and overs, the overs are treated to produce a partially hydrolyzed biomass, and the partially hydrolyzed biomass and the unders are anaerobically digested. Treating the overs includes fermenting and mixing the overs with an aerotolerant anaerobic bacteria in a controlled environment, such as a rotating drum, while air is passed through the controlled environment. The moisture content, pH, and biological content of the overs can be adjusted before the overs are treated. Volatile fatty acids from the air passed through the controlled environment can be collected for anaerobic digestion or can be recirculated back into the controlled environment. The cleansed air can also be recycled back into the controlled environment.

19 Claims, 8 Drawing Sheets

U.S. PATENT DOCUMENTS

| | | |
|---|---|---|
| 4,935,038 A | 6/1990 | Wolf |
| 4,971,616 A | 11/1990 | Glogowski |
| 4,974,781 A | 12/1990 | Placzek |
| 4,983,296 A | 1/1991 | McMahon et al. |
| 5,047,349 A | 9/1991 | Eweson |
| 5,204,263 A | 4/1993 | Finn |
| 5,206,173 A | 4/1993 | Finn |
| 5,215,921 A | 6/1993 | Finn |
| 5,244,804 A | 9/1993 | Horkan et al. |
| 5,250,100 A | 10/1993 | Armbristor |
| 5,253,764 A | 10/1993 | Gement |
| 5,254,472 A | 10/1993 | Brooks, III et al. |
| 5,322,792 A | 6/1994 | Peguy |
| 5,348,236 A | 9/1994 | Spargo et al. |
| 5,377,917 A | 1/1995 | Wiljan et al. |
| 5,407,809 A | 4/1995 | Finn |
| 5,437,374 A | 8/1995 | Bills et al. |
| 5,445,329 A | 8/1995 | Anderson |
| 5,529,692 A | 8/1995 | Anderson |
| 5,459,071 A | 10/1995 | Finn |
| 5,461,843 A | 10/1995 | Garvin et al. |
| 5,500,306 A | 3/1996 | Hsu et al. |
| 5,507,396 A | 4/1996 | Hauch |
| 5,522,913 A | 6/1996 | Peguy |
| 5,540,391 A | 7/1996 | Anderson |
| 5,556,445 A | 9/1996 | Quinn et al. |
| 5,566,532 A | 10/1996 | Inman et al. |
| 5,583,045 A | 12/1996 | Finn |
| 5,655,718 A | 8/1997 | Anderson |
| 5,661,031 A | 8/1997 | Murphy et al. |
| 5,700,687 A | 12/1997 | Finn |
| 5,724,793 A | 3/1998 | Inman et al. |
| 5,758,462 A | 6/1998 | Finn |
| 5,782,950 A | 7/1998 | Kanitz et al. |
| 5,795,479 A | 8/1998 | Vogt et al. |
| 5,821,111 A | 10/1998 | Grady et al. |
| 5,972,696 A | 10/1999 | Lipsey |
| 6,003,680 A | 12/1999 | Finn |
| 6,048,458 A | 4/2000 | Vogt et al. |
| 6,050,423 A | 4/2000 | Dunnuck et al. |
| 6,062,004 A | 5/2000 | Inman et al. |
| 6,087,159 A | 7/2000 | Finn |
| 6,113,786 A | 9/2000 | Burke |
| 6,136,577 A | 10/2000 | Gaddy |
| 6,202,389 B1 | 3/2001 | Inman et al. |
| 6,240,980 B1 | 6/2001 | Inman et al. |
| 6,267,309 B1 | 7/2001 | Chieffalo et al. |
| 6,299,774 B1 | 10/2001 | Ainsworth et al. |
| 6,306,248 B1 | 10/2001 | Eley |
| 6,309,547 B1 | 10/2001 | Burke |
| 6,312,649 B2 | 11/2001 | Finn |
| 6,337,203 B1 | 1/2002 | Beaulieu |
| 6,340,581 B1 | 1/2002 | Gaddy |
| 6,342,378 B1 | 1/2002 | Zhang et al. |
| 6,379,505 B1 | 4/2002 | Wiljan et al. |
| 6,397,492 B1 | 6/2002 | Malley |
| 6,413,364 B1 | 7/2002 | Sandison |
| 6,516,590 B2 | 2/2003 | Inman et al. |
| 6,578,783 B2 | 6/2003 | Simon et al. |
| 6,592,250 B1 | 7/2003 | Gement |
| 6,709,500 B1 | 3/2004 | West |
| 6,730,223 B1 | 5/2004 | Anderson et al. |
| 6,905,600 B2 | 6/2005 | Lee, Jr. |
| 7,015,028 B2 | 3/2006 | Choate et al. |
| 2001/0048093 A1 | 12/2001 | Bachnak |
| 2002/0022260 A1 | 2/2002 | Ishii |
| 2002/0079266 A1 | 6/2002 | Ainsworth et al. |
| 2002/0148778 A1 | 10/2002 | Raven |
| 2002/0182710 A1 | 12/2002 | Horn et al. |
| 2003/0066322 A1 | 4/2003 | Perriello |
| 2003/0121851 A1 | 7/2003 | Lee, Jr. |
| 2003/0180940 A1 | 9/2003 | Watson et al. |
| 2003/0213859 A1 | 11/2003 | Simon et al. |
| 2004/0000179 A1 | 1/2004 | Hiraki |
| 2004/0123637 A1 | 7/2004 | Rostrom |
| 2004/0191755 A1 | 9/2004 | Kemper et al. |
| 2005/0000906 A1 | 1/2005 | Blais et al. |
| 2005/0035058 A1 | 2/2005 | Forrestal et al. |
| 2005/0044911 A1 | 3/2005 | Shimose |
| 2005/0051646 A1 | 3/2005 | Horne |
| 2005/0089998 A1 | 4/2005 | Miller |
| 2005/0106715 A1 | 5/2005 | Niv et al. |
| 2005/0112741 A1 | 5/2005 | Kohr |
| 2005/0126957 A1 | 6/2005 | Porter et al. |
| 2005/0134102 A1 | 6/2005 | Cymerman et al. |
| 2005/0199028 A1 | 9/2005 | Shin |
| 2006/0065608 A1 | 3/2006 | Choate et al. |
| 2006/0124559 A1 | 6/2006 | Choate et al. |

FOREIGN PATENT DOCUMENTS

| | | |
|---|---|---|
| DE | 10336209 | 3/2005 |
| WO | WO-88/08030 | 10/1988 |
| WO | WO-98/00558 A1 | 1/1998 |
| WO | WO-99/25460 A1 | 5/1999 |
| WO | WO-99/35107 | 7/1999 |
| WO | WO-00/68407 | 11/2000 |
| WO | WO-02/08438 A2 | 1/2002 |
| WO | WO-02/15945 | 2/2002 |
| WO | WO-02/36502 | 5/2002 |
| WO | WO-02/062497 | 8/2002 |
| WO | WO-02/070635 | 9/2002 |
| WO | WO-02/083601 | 10/2002 |
| WO | WO-03/043957 | 5/2003 |
| WO | WO-03/090894 A1 | 11/2003 |
| WO | WO-2004/058424 | 7/2004 |
| WO | WO-2004/060587 | 7/2004 |
| WO | WO-2004/076082 | 9/2004 |
| WO | WO-2004/085019 | 10/2004 |
| WO | WO-2005/063946 | 7/2005 |

OTHER PUBLICATIONS

Swartzbaugh, J.T. et al. "Recycling Equipment and Technology for Municipal Solid Waste", 1993, 150 pages.

SYSTEMS AND PROCESSES FOR TREATMENT OF ORGANIC WASTE MATERIALS WITH A BIOMIXER

CROSS-REFERENCE TO RELATED APPLICATIONS

This application is a Continuation-In-Part of co-pending U.S. application Ser. No. 11/385,098 filed on Mar. 20, 2006 and entitled "Systems and Methods for Treatment of Organic Waste Materials," which is a Continuation-In-Part of U.S. application Ser. No. 10/427,454, filed Apr. 30, 2003 now U.S. Pat. No. 7,015,028 issued on Mar. 21, 2006, and claims the benefit of both pursuant to 35 U.S.C. §120; this application also claims the benefit of U.S. Provisional Patent Application No. 60/749,352 filed on Dec. 9, 2005 and entitled "Biomass Production from Waste Material for Energy Generation" which is incorporated herein by reference in its entirety. This application is related to U.S. application Ser. No. 11/031,218 filed on Jan. 6, 2005, now U.S. Pat. No. 7,316,921 and entitled "Organic Waste Material Treatment System," which is a divisional application of U.S. application Ser. No. 10/427,454.

BACKGROUND OF THE INVENTION

1. Field of the Invention

The present invention relates generally to processing of waste materials, and more particularly to systems and processes for handling organic waste materials.

2. Description of the Prior Art

Landfilling has traditionally been the method of waste handling, but landfilling can cause environmentally unacceptable pollution discharges to the water and, as real estate values increase, is considered to be an unattractive use of land. Thus, current waste management strategies seek to limit the amount of refuse directed to landfills. Recycling and composting programs have become widely accepted for both commercial and residential waste to reduce the demands on landfills.

Generally, recycling programs require separating the waste by type, either at a point of collection (source separated) or further along, such as at a transfer station. Recyclable components can include glass, metals, and plastics, while compostable components can include agricultural wastes, plant matter, food stuffs, wood, cardboard, and paper. Once separated, waste materials are commonly referred to as "source separated," and source separated materials that are collected together from separate collection points constitute a "single stream."

Compost facilities have been built to process non-recyclable waste, either in the form of municipal solid waste with provisions for contamination removal, or source separated organic waste. An alternative to composting for non-recyclable waste streams are refuse-to-energy plants where material is burned to create energy. Refuse-to-energy plants first process waste by grinding and then burning the ground material. Although efforts are made to separate out hazardous materials from the waste stream, these plants have had a history of emissions and operational problems related to contaminants. The residual ash created from this burning has also, in some cases, been found to be hazardous.

Anaerobic digestion presents another alternative for handling organic waste materials. The primary objective of anaerobic digestion is the production of a mixture of hydrocarbon gases ("biogas"), which may be utilized as an energy source to generate electricity and/or heat. Any solid material remaining at the completion of the anaerobic digestion process is typically disposed of by conventional landfilling or composted into a soil amendment.

Because of the high capital costs associated with anaerobic digestion equipment, and the environmental issues associated with refuse-to-energy plants, composting has become the dominant method in the United States for the management and re-use of organic waste materials generated in rural and suburban settings. The growing use of composting as a preferred alternative to disposal of organic waste material has also created some environmental problems. These problems include emissions of noxious gases and ozone pre-cursors, runoff from the compost facility, and high energy consumption during material processing. These problems may become particularly acute if the organic waste material contains large amounts of food waste or other high moisture content waste.

Commercial-scale composting is also subject to a variety of financial considerations including capital investment related to accommodating peak seasonal feedstock deliveries, compost process time, and controlling the timing of compost production to match the seasonal demand of the agricultural industry and other compost buyers. Further, the compost produced by these facilities is a low-value product, therefore municipalities have to pay to have the waste accepted.

SUMMARY

In an exemplary embodiment of the invention, organic waste materials are treated via a multi-stage process involving anaerobic hydrolysis, anaerobic digestion of the liquid hydrolysis product, and aerobic composting of the solids remaining after hydrolysis. The organic waste materials may be pre-treated by adding an amount of a liquid inoculant sufficient to raise the moisture content of the organic waste to a minimum of sixty percent. The organic waste material is then placed within a sealed hydrolysis vessel, which takes the form of a cylindrical polymer bag in some embodiments. Hydrolysis of the organic matter within the vessel results in the production of a liquid product, which is removed from the vessel via a conduit that communicates with the vessel's interior. Removal of the liquid may be performed either continuously, at specified intervals, or at the completion of the hydrolysis process.

The liquid hydrolysis product transferred from the vessel, which may be temporarily stored in a holding tank, is passed to a conventional anaerobic digester. In a thermophilic digester, methanogenic bacteria convert organic matter that is dissolved and/or suspended in the liquid hydrolysis product to a biogas product. The biogas product may be combusted prior to release to the atmosphere in order to reduce or eliminate emissions of flammable or otherwise objectionable gaseous species, such as methane. Thermal energy produced by combustion of the biogas may be utilized to supply heat and/or electrical power for processing operations. The liquid digester product remaining after completion of the digestion process can be removed from the digester and employed as inoculant for hydrolysis of subsequently processed organic waste material.

After completion of hydrolysis, the remaining solid waste material may be removed from the vessel and composted under aerobic conditions. The composting process may be implemented as a static reversed air aerobic composting system, wherein the solid waste material is placed in a pile atop a pad adapted with an array of ports that communicate with a manifold. A blower, coupled to the manifold, draws ambient air through the solid waste material, through the ports, and into the manifold. The ambient air drawn into the manifold is passed through a biofilter to remove undesirable species before being discharged back to the atmosphere. Alternatively, after completion of hydrolysis, the remaining solid waste material may be composted using an aerobic static pile ("windrow") process, positive or negative aerated static pile or other suitable process. The end result of the composting process is a decomposed material that may be used as a soil amendment.

The foregoing waste material treatment processes present several advantages over prior art techniques including the reduction of emissions of ozone precursors and other noxious or otherwise objectionable gases, lowering the net energy requirements associated with the composting process, and the ability to rapidly and inexpensively scale to meet peak throughput demands by adjusting the number and capacity of the relatively low-cost hydrolysis vessels.

In other exemplary embodiments of the invention, waste material is treated by screening the material to produce "unders" and "overs." The overs are hydrothermally treated to produce a partially hydrolyzed biomass, and the unders and the partially hydrolyzed biomass are anaerobically digested. The waste material can be a source separated organic waste or municipal solid waste, for example. In some embodiments, hydrothermally treating the overs includes mechanical mixing of the overs in an autoclave. Hydrothermally treating the overs can also include recovering volatile organic compounds. In these latter embodiments, hydrolyzing the partially hydrolyzed biomass and the unders of the waste material can include hydrolyzing the volatile organic compounds.

Some additional embodiments include sorting the waste material prior to screening the waste material, while other embodiments include sorting the overs after screening the waste material. Here, sorting is used to remove certain types of materials, such as recyclable materials and hazardous materials, from the waste material. The moisture content of the overs can be adjusted, in some embodiments, before hydrothermally treating the overs. Further, the partially hydrolyzed biomass can be screened to produce unders and overs thereof, where the unders are anaerobically digested. In these embodiments, the overs of the partially hydrolyzed biomass can also be sorted.

In another exemplary process for treating waste material, waste material is hydrothermally treated with steam to produce a partially hydrolyzed biomass, volatile organic compounds are recovered from the steam, and the partially hydrolyzed biomass and the volatile organic compounds are anaerobically digested. The method can further comprise screening the waste material to produce unders and overs thereof, and anaerobically digesting the unders. In some embodiments the partially hydrolyzed biomass is screened to produce unders and overs thereof, and the unders of the partially hydrolyzed biomass are anaerobically digested. In these latter embodiments, the method can also comprise sorting the overs of the partially hydrolyzed biomass.

An exemplary system for treating waste material comprises a screening device, an autoclave, and a digester. The screening device separates the waste material into unders and overs, the autoclave is configured to receive the overs from the screening device and to process the overs with steam to produce a partially hydrolyzed biomass, and the digester is configured to receive the unders of the waste material and the partially hydrolyzed biomass. The digester can comprise, for example, a two-stage anaerobic digester. An exemplary screening device is a trommel. Additional embodiments include a mixer and infeed system disposed between the screening device and the autoclave. Still other embodiments comprise an eductor coupled to the autoclave and configured to discharge to the digester.

In still another exemplary process for treating waste material, the waste material is screened to produce unders and overs, the overs are treated to produce a partially hydrolyzed biomass, and the partially hydrolyzed biomass and the unders are anaerobically digested. Treating the overs includes fermenting and mixing the overs with an aerotolerant anaerobic bacteria in a controlled environment, such as a rotating drum, while air is passed through the controlled environment.

Some embodiments of this process further comprise adjusting the overs of the waste material before treating the overs. For example, the moisture content and pH of the overs can both be adjusted. Additionally, a biological content of the overs can be adjusted by adding a portion of the partially hydrolyzed biomass back into the overs. In additional embodiments the process further comprises recovering volatile fatty acids from the air passed through the controlled environment, for example, by scrubbing the air with water to cleanse the air and to concentrate the volatile fatty acids in the water. In some of these embodiments the process further comprises anaerobically digesting the volatile fatty acids, or adding the water containing the volatile fatty acids back into the controlled environment. In some other embodiments, the cleansed air is recycled back into the controlled environment.

Still another exemplary system for treating waste material comprises a screening device for separating the waste material into unders and overs, a rotatable drum, and an air system including an air injector configured to inject air into a discharge end of the drum, and an air collection device configured to receive the air from a feed end of the drum. The drum is sloped relative to the horizontal and configured to receive the overs from the screening device and to mix the overs with an aerotolerant anaerobic bacteria to produce a partially hydrolyzed biomass. In some embodiments the system further comprises a water scrubbing system configured to receive the air from the air collection device and to cleanse the air with water. The air injector, in some of these embodiments, is configured to receive the cleansed air from the water scrubbing system and inject the cleansed air into the drum. The system can also comprise an infeed system configured to receive water from the water scrubbing system and to mix the water into the overs.

DETAILED DESCRIPTION

Figure 1:
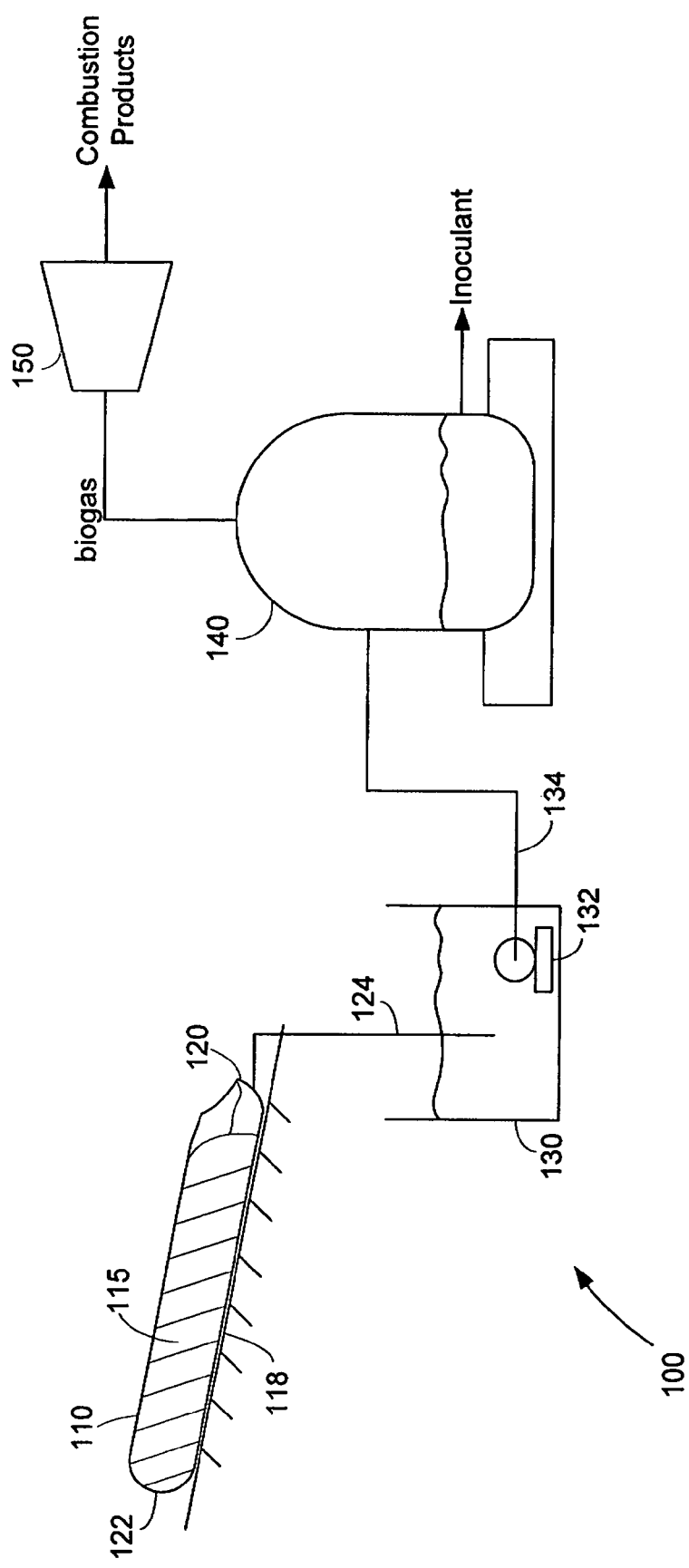
FIG. 1 is a symbolic diagram of an organic waste treatment system in accordance with an embodiment of the invention.

FIG. 1 symbolically depicts the major components of an organic waste treatment system 100 implemented in accordance with an exemplary embodiment of the invention. A flexible hydrolysis vessel 110 contains a volume of an organic waste material 115 having a relatively high moisture content and density. The hydrolysis vessel 110 has pliable walls formed from a polymer or other material that is substantially impermeable to gases and liquids. The ends of vessel 110 are closed and sealed to provide an anaerobic environment for the hydrolysis of the organic waste material 115. Details regarding the construction of vessel 100 are set forth below in connection with FIG. 2.

The vessel 110 rests on a supporting surface 118, which is sloped along the longitudinal axis of vessel 110 such that the bottom portion of a first end 120 of the vessel 110 is situated lower than the bottom portion of the opposite end 122 of the vessel. This condition causes liquids produced during the anaerobic hydrolysis of the organic waste material 115 to flow under the influence of gravity to a region of the vessel interior proximate to the first end 120. As described below in connection with FIG. 2, liquid flow within vessel 110 may be facilitated by placement of one or more perforated pipe structures within the vessel 110.

At the completion of the anaerobic hydrolysis process, or at specified intervals during the anaerobic hydrolysis process, collected liquid (including dissolved and suspended organic compounds) is removed from the interior of the vessel 110 via a conduit 124. The conduit 124 can comprise a pipe formed from a suitable material, such as polyvinyl chloride (PVC), that is resistant to attack by organic acids and other corrosive compounds that can be contained within the hydrolysis liquids. A valve (not shown in FIG. 1) integrated with, or located exterior to the vessel 110, can be opened to effect flow of the collected liquid out of the vessel. The liquid flows through the conduit 124 and, in some embodiments, into a holding tank 130. The holding tank 130 can serve as a reservoir to store the liquid until a digester 140 is available for further processing. When digester 140 becomes available, a suitable quantity of liquid is pumped by pump 132 from the holding tank 130 through a line 134 into the digester 140.

The digester 140 can be in the form of a conventional closed digester vessel in which the hydrolysis liquid product is combined with methane-producing bacteria and incubated for a predetermined period to produce biogas and a liquid digester product (inoculant). The interior of digester 140 can be adapted with conventional membranes, heaters, and other structures, as appropriate, to facilitate and optimize the digestion process. Digesters of this general description are available from industrial suppliers such as Onsite Power Systems, Inc. of Camarillo, Calif.

The biogas is preferably combusted prior to release to the atmosphere to destroy methane (a primary component of the biogas) and other flammable, noxious, and other species for which emission to the environment is undesirable, dangerous, and/or regulated. Thermal energy produced by combustion of the biogas may be utilized for various purposes, including electrical power generation, which may in turn be used to drive various components of the waste treatment system 100, including blowers and pumps. An electrical generator 150 (which may comprise, for example, a conventional turbine generator or microturbine) can be provided for this purpose. Additionally, hot exhaust gases resulting from the biogas combustion can be passed through a heat exchanger (not shown) to produce heated air and/or liquid streams for use in the digester 140 or in other components of the waste treatment system 100, or in related apparatus. The exhaust gases from biogas combustion can be subjected to filtration and/or other pollutant control processes, as appropriate, prior to atmospheric venting. In yet another alternative embodiment, the biogas is processed and refrigerated to produce liquid natural gas (LNG), which may be stored or shipped offsite for use as an energy source.

While the system 100 is depicted as having a single hydrolysis vessel 110 and digester 140, those skilled in the art will recognize that commercial implementations may include any number of hydrolysis vessels and digesters, as suited to a specific application and required throughput. Multiple hydrolysis vessels 110 and/or digesters 140 can be arranged and linked in various suitable arrangements. For example, multiple hydrolysis vessels 110 may be arranged in parallel to supply liquid to a single holding tank 130 and digester 140. Alternatively, multiple hydrolysis vessels 110 may be coupled to a plurality of digesters 140, each of which may be brought on-line or off-line as appropriate according to throughput and maintenance requirements.

Figure 2:
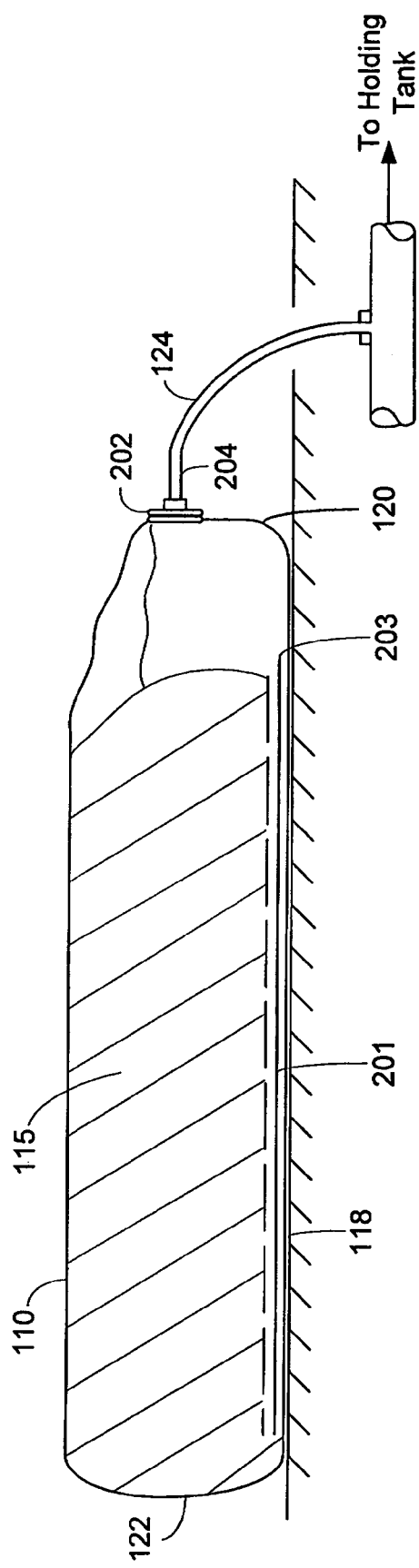
FIG. 2 is a symbolic longitudinal cross-sectional view of the flexible hydrolysis vessel of the system of FIG. 1.

FIG. 2 is a longitudinal cross-sectional view depicting the anaerobic hydrolysis vessel 110. In some embodiments t vessel 110 takes the form of an elongated, generally cylindrical container having thin walls formed from a polymer material. Desirable properties of the polymer material include impermeability to gases and liquids, high resilience (to avoid tearing), and high resistance to chemical attack from organic acids and other compounds formed during hydrolysis. Containers of this general description are available from commercial suppliers such as Ag-Bag International Limited of Warrenton, Oreg. The dimensions of the vessel 110 may be selected in view of the required throughput, structural integrity, and space considerations. In an exemplary commercial implementation, vessel 110 has a diameter of approximately five to ten feet, and a length in the range of 100-200 feet. Initially, at least one end of the vessel 110 is left open to enable placement of the organic waste material 115 into the vessel 110. As described below in connection with FIG. 3, filling of vessel 110 can be accomplished using a conventional bagging machine.

As also shown in FIG. 2, one or more perforated drainage pipes 201 can be placed within the interior of vessel 110 to facilitate the flow of liquids generated during the hydrolysis process to the first (lower) end of the vessel. Pipe 201 is located at or near the bottom portion of the interior and traverses substantially the length of the vessel 110. Liquids that enter the pipe 201 through perforations in the pipe wall exit the pipe 201 at a mouth 203 opening to the unfilled region of the vessel 110 adjacent to the vessel's lower end 120. Placement of the perforated pipe 201 within the vessel 110 can be accomplished by employing an apparatus and method substantially similar to that described in U.S. Pat. No. 5,461, 843 ("Method for Treatment of Bagged Organic Materials" by Garvin et al.).

Vessel 110 is further adapted with a port 202 located proximate to the first (lower) end 120 to enable removal of the hydrolysis liquid product. The port 202 is coupled to the conduit 124 by a flange 204 so that accumulated liquids flow into the conduit 124 to the holding tank 130. Vessel 110 can be coupled to the conduit 124 throughout the hydrolysis stage to continuously withdraw the hydrolysis liquid. Alternatively, the conduit 124 can be coupled to vessel 110 only when drainage of the hydrolysis liquid is desired, such as at periodic intervals or at the completion of the hydrolysis process. One or more valves, which may be integrated with the port 202, or located externally thereto, can be provided for this purpose.

Figure 3:
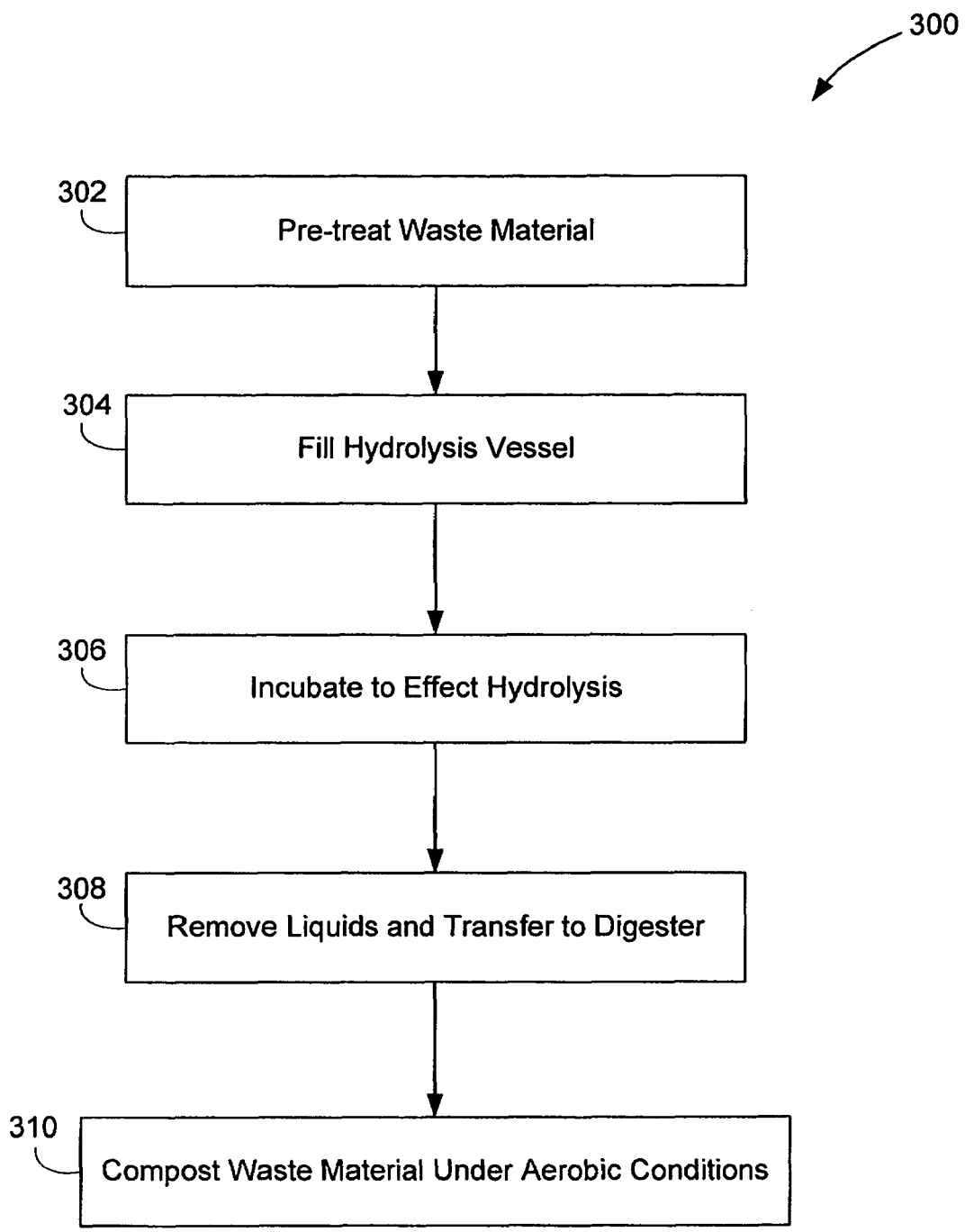
FIG. 3 is a flowchart depicting a process for treating organic waste material, in accordance with an embodiment of the invention.

FIG. 3 depicts an exemplary process for treating organic waste material 115 in accordance with an embodiment of the invention. Although the process 300 is described below in terms of its application to the exemplary waste treatment system 100, the process should not be construed as being limited to implementing the system in the FIG. 1. In an optional step 302, the organic waste material 115 is pretreated prior to placement within the vessel 110. The organic waste material 115 can comprise multiple waste streams, including without limitation agricultural waste, food waste, residential lawn/garden waste, and cannery waste. The pretreatment step 302 can include blending of two or more of these waste streams. The blending proportions (percentages of each waste stream in the organic waste material) can be adjusted to optimize various properties of the organic waste material, such as the carbon to nitrogen ratio. The blended material can then be processed to reduce the average particle size and increase the surface area available for reaction. Such processing can include, for example, crushing, grinding, or shredding. According to one implementation, the waste material 115 is ground to a maximum particle size (longest dimension) of 1.5 inches.

The pre-treatment step 302 may further include the addition of a liquid inoculant to the waste material. The addition of the inoculant supplies the anaerobic bacteria required for the hydrolysis reactions to occur and can also be used to increase the moisture content of the waste material. Inoculant is available in bulk from commercial suppliers; however, according to a preferred implementation, the inoculant is wholly or partially comprised of the liquid digester product produced by digestion of a previously processed batch of organic waste material. Use of the liquid digester product as the inoculant confers a substantial economic benefit by removing the need to purchase commercial inoculant and additionally avoids the costs associated with disposal/treatment of the liquid digester product. The amount of inoculant added to the organic waste material 115 should be sufficient to raise the moisture content to at least (and preferably significantly greater than) sixty percent by weight. The resultant organic waste material 115 will typically have a density of approximately 800-1000 pounds/cubic yard.

Next, in a step 304, the pretreated organic waste is placed within the vessel 110. Placement of the waste within the vessel 110 can be achieved by employing a bagging machine of the type described in U.S. Pat. No. 5,566,532 and sold by Ag-Bag International Limited. Generally, such machines include a conveyor for transferring material from a hopper into a feed tunnel, and a rotor for compressing the material and propelling the compressed material into an elongated bag having an open end affixed to the tunnel exit. A bagging machine can further include a ram that is temporarily inserted within the interior of the vessel 110 to push the waste material 115 along the length of the vessel 110. As depicted in FIG. 2, the entire interior volume of vessel 110 is filled with organic waste material 115 except for a region adjacent to the first (lower) end 120, which is left unfilled to accommodate the liquid product that is generated by the hydrolysis of the waste material 115. In a typical implementation utilizing a vessel having a length of 200 feet, the unfilled region will have a length of approximately 10 feet. The vessel 110 is sealed at the completion of filling step 304 to create an anaerobic environment for hydrolysis of the organic waste material 115. Prior to sealing, air remaining in the bag can optionally be removed using a vacuum pump (not shown) in order to reduce the oxygen concentration within the vessel 110.

The organic waste material 115 is then incubated in a step 306 within the sealed vessel 110 for a specified period. During this period, the organic waste material 115 undergoes hydrolysis, wherein bacteria or other agents convert a portion of the hydrocarbon compounds in the waste material 115 to organic acids, alcohols, and/or aldehydes. Hydrolysis of the organic waste material 115 results in the production of a liquid hydrolysis product, which flows under gravity to the unfilled region of vessel 110. The liquid hydrolysis product contains suspended and dissolved organic compounds, as well as dissolved gases. Removal of these compounds from the organic waste material 115 during the hydrolysis process may substantially reduce emissions of ozone precursors and noxious gases produced in the subsequent composting phase. The time period during which organic waste material 115 undergoes hydrolysis will vary according to feedstock composition, temperature, and digester requirements, but will typically be on the order of three weeks. It is noted that the organic waste material 115 may be stored within vessel 110 for a longer period of time in order to match production of the compost end product to seasonal demand.

Next, in a step 308, the accumulated liquid hydrolysis product is removed from the interior of the vessel 110 and transferred through the conduit 124 to the holding tank 130. Removal and transfer of the liquid hydrolysis product can be performed continuously, at predetermined intervals during hydrolysis, or after the completion of hydrolysis. If removal and transfer of the liquids is performed intermittently, flow of the liquid from the vessel 110 interior may be controlled by a valve associated with the port 202 or the conduit 124. The liquid hydrolysis product is subsequently pumped into the digester 140 and incubated under anaerobic conditions to produce a biogas product and a liquid product, which may be used as an inoculant in the manner described above.

Figure 4:
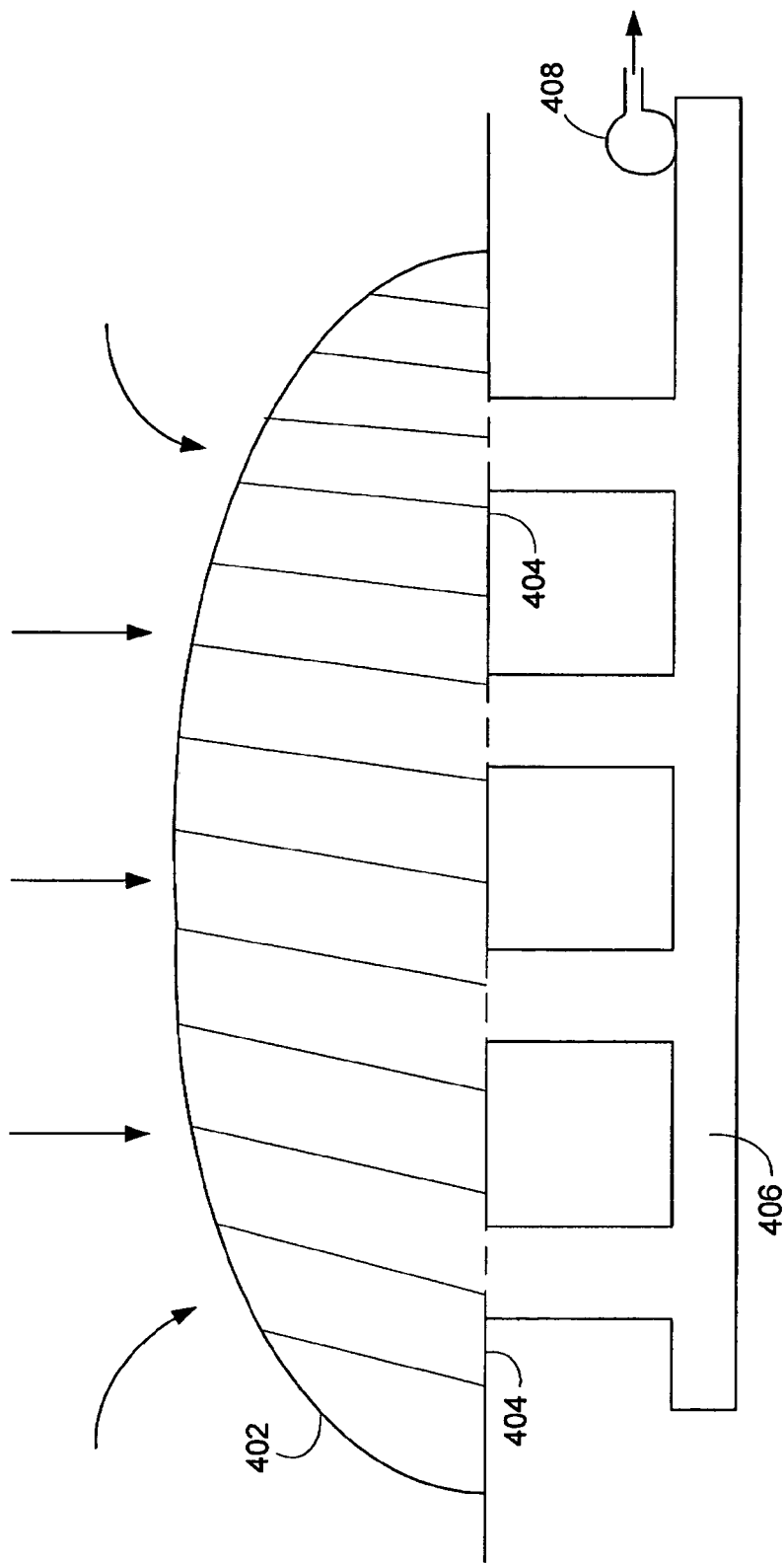
FIG. 4 is a symbolic side view of an apparatus for static reverse air composting, in accordance with a specific implementation of the invention.

In a step 310, the organic material 115 is removed from the vessel 110 and subjected to further decomposition under aerobic conditions. This step may be implemented, for example, as a static reverse air aerobic decomposition process. In this process, which is illustrated by FIG. 4, the organic waste material is arranged in a pile 402 atop a supporting pad adapted with an array of air ports 404 distributed along the length and/or across the width of the pile 402. The outer periphery of the pile 402 is exposed to the atmosphere. The air ports 404 communicate with at least one manifold 406. A blower 408, or similar device, reduces the pressure within the manifold 406 to below ambient pressure. The resultant pressure gradient draws ambient air through the pile 402, through the air ports 404, and into the manifold 406. This action provides a flow of air into the interior of the pile 402 to facilitate aerobic decomposition reactions. The air drawn through manifold 406 is preferably passed through a biofilter to remove objectionable gas components prior to venting the air stream back to the atmosphere. Step 310 can be alternatively implemented by employing any one of a number of suitable prior art techniques, such as the forced-air composting process described in the aforementioned U.S. Pat. No. 5,461,843 or any conventional windrow-based process.

By utilizing the processes discussed above, a high-quality compost may be advantageously derived from food waste and other high moisture content feedstocks while avoiding the environmental problems of traditional composting methods and the need for large capital expenditures associated with conventional hydrolysis equipment. It should be noted that the process and system described above can be advantageously applied to a wide range of organic waste materials, including without limitation municipal solid waste (MSW), biosolids, sludge, agricultural wastes, cannery wastes, manures, green and wood wastes, and other waste streams having organic content.

Figure 5:
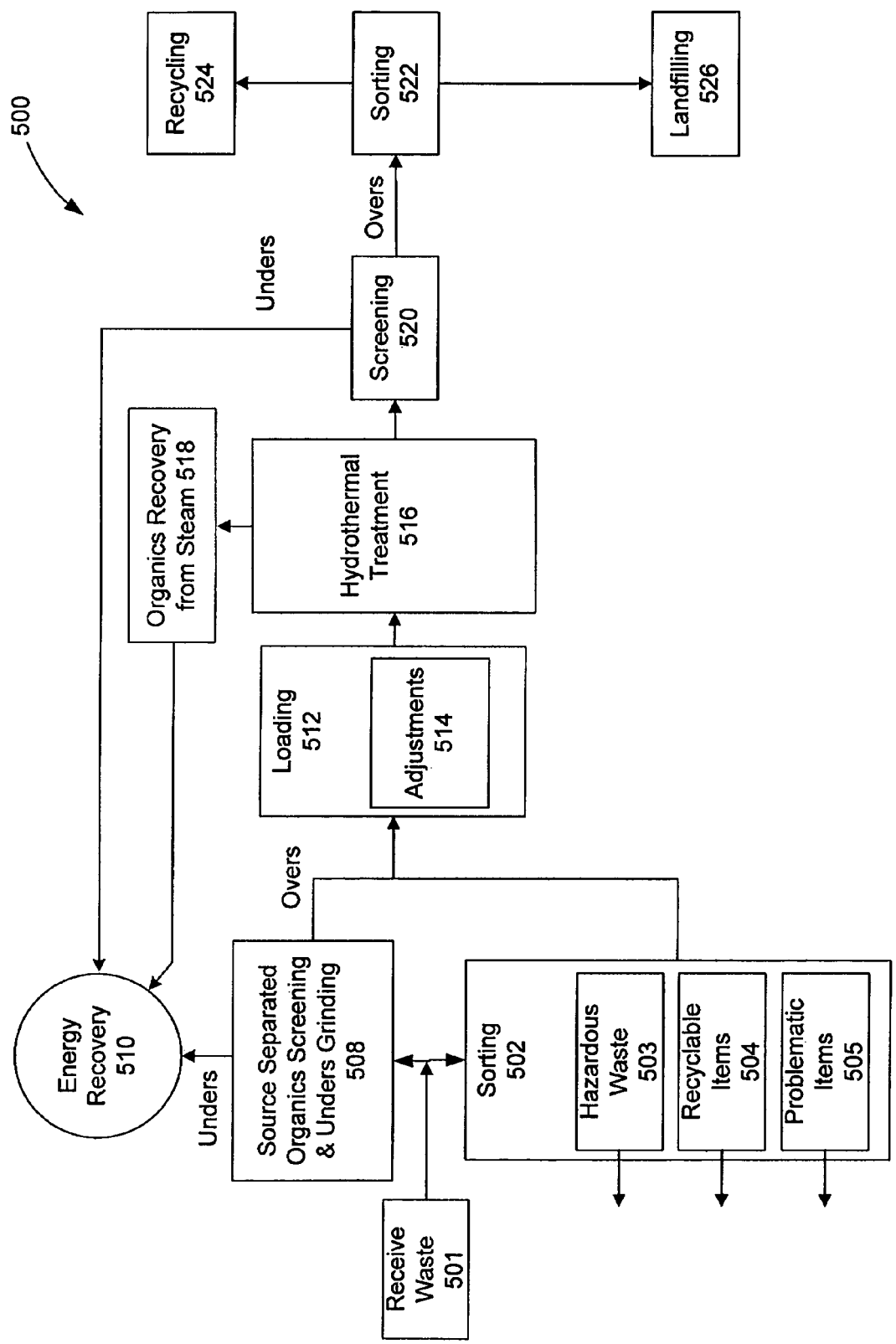
FIG. 5 is a flow diagram of a process for treating waste material in accordance with a specific implementation of the invention.

Further embodiments of the present invention are described with reference to FIGS. 5 and 6. In the embodiments described above, hydrolysis in the vessel 110 proceeds typically over the span of weeks or more. While this is acceptable in some circumstances, in other situations much faster processing is desirable. As described below, an autoclave can be employed to accelerate the hydrolysis of organic waste material. FIG. 5 shows a flow diagram for an exemplary process 500, while FIG. 6 depicts the major components of an organic waste treatment system 600 implemented in accordance with the process 500.

Figure 6:
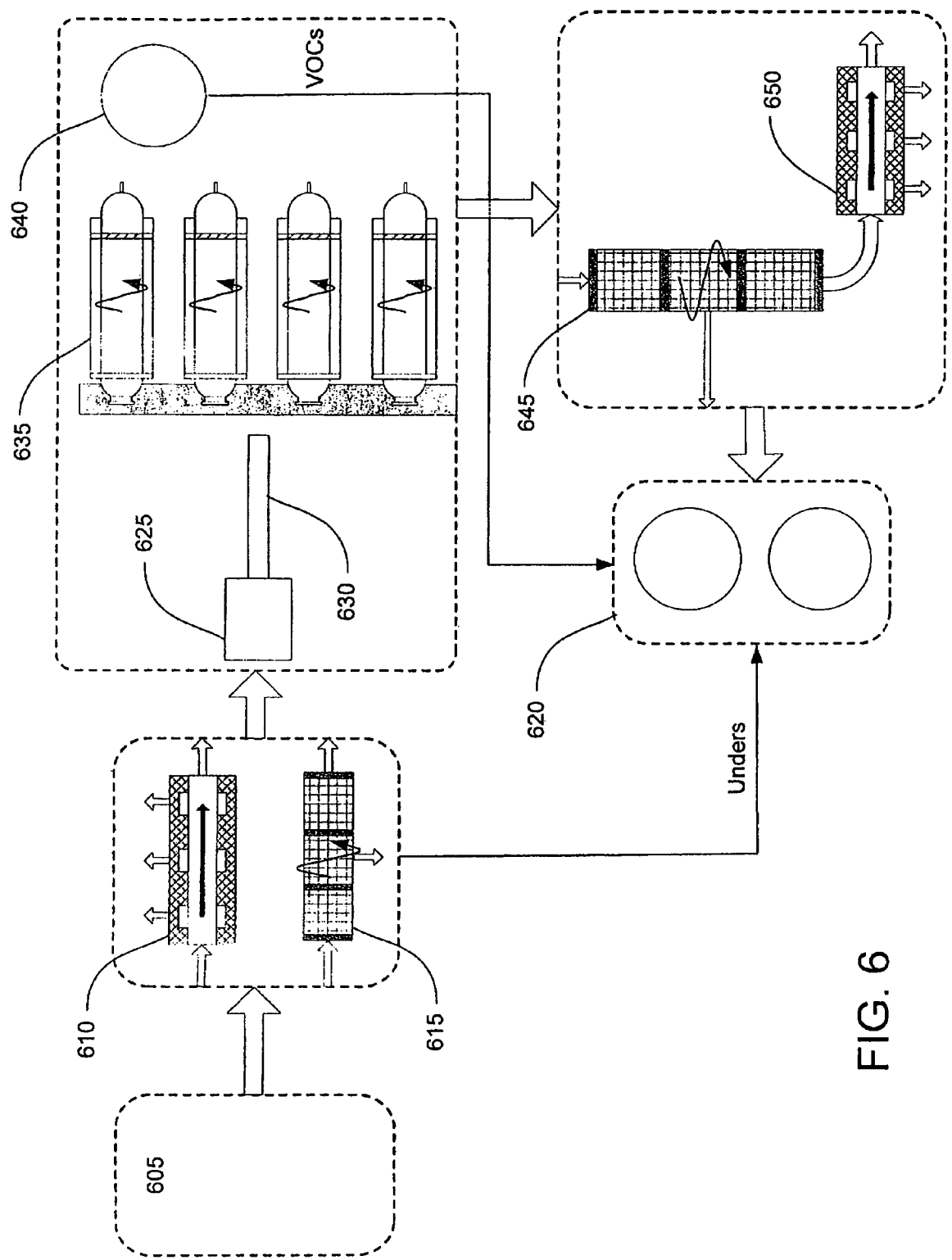
FIG. 6 depicts major components of an organic waste treatment system in accordance with a specific implementation of the invention.

With reference to both FIGS. 5 and 6, an initial waste material is received 501, for example, on a tipping or sorting floor 605. Depending on the source of the waste material, the waste material can be sorted 502 to remove various unsuitable materials that typically fall into three categories, hazardous waste, recyclable items, and problematic items. The sorting 502 can be performed either on the sorting floor 605 or in a sorting line 610, depending on the quantity and quality of the initial waste material.

Sorting to remove hazardous waste 503, such as batteries, pesticides, and paint, removes materials that would otherwise contaminate the end product or pose worker safety problems. Recyclable items such as glass, certain plastics, and certain metals, are removed 504 and directed to appropriate recycling facilities. Problematic items are removed 505 that can interfere with the operation of down-stream processes such as screening and autoclaving. One type of problematic material includes those objects that can wrap around other materials while in a rotating drum environment, for instance, rope, hose, and clothing. Buckets and other large items can also be problematic. Additionally, lumber generally cannot be hydrolyzed within the time constraints of the autoclave process, and therefore is also removed.

It will be appreciated that sorting 502 is not essential where the initial waste material is known to already be substantially free of deleterious materials, though sorting 502 can still be performed. For example, where the initial waste material is a source separated organic waste material, the amounts of the hazardous, recyclable, and problematic items are typically small and can alternately be addressed by screening 508. Screening 508 can be accomplished with a screening device 615 such as one or more trommels. A suitable screen size for the screening device 615 is in the range of ½" to 2".

Screening 508 is primarily used, however, to classify the waste material into "unders" and "overs," those particles that have either passed through a screen with a particular mesh size, or have not passed through the screen. The unders, which include a disproportionate weight fraction of the total moisture in the waste material, can be further ground or macerated into a pulp and transferred to an energy recovery process 510. An anaerobic digestion system 620 for energy recovery 510 is shown in FIG. 6 and described in more detail below. Removing the unders from the waste material reduces the amount of waste material that is directed to subsequent processing and reduces the moisture content of that waste material. Where the initial waste material is a source separated organic waste, food waste can comprise a substantial fraction of the unders.

As noted, the overs from the screening 508 are further processed. In some embodiments that do not include sorting 502, the overs can include unsuitable materials, like recyclable items, that will be removed from the waste material only after further processing. After screening 508, the overs are directed to a loading process 512. Here, the composition of the waste material can optionally be adjusted 514 as needed to obtain a more optimal mixture for further processing. For instance, drier material such as paper can be added where the moisture content of the overs is too high. Alternately, wetter materials or water can be added to the overs to increase moisture content. A moisture content of about 60% is considered optimal but potentially the optimal moisture content may be between 50% and 65%. Similarly, other materials can be added as needed to adjust the pH and the composition of the waste material.

In FIG. 6, the loading process 512 is performed by an optional mixer 625 (for adjusting 514 the waste material) and an infeed system 630. It is noted that water, or other materials, can also be added to the waste material while in the infeed system 630. This can be done to either make additional adjustments 514 after processing in the mixer 625, or in the alternative, to increase the moisture content of the waste material without using the mixer 625. The infeed system 630 transfers the waste material to a hydrothermal treatment 516, represented in FIG. 6 by one or more autoclaves 635, through the use of a gravity conveyor'system and/or a mechanical ram, for example.

The hydrothermal treatment 516 reduces the waste material to a useable biomass by using mechanical mixing and steam under conditions of elevated temperature and pressure. In some embodiments, the useable biomass is produced with a uniform pulp consistency. Also in some embodiments, the hydrothermal treatment 516 does not fully hydrolyze the cellulose in the waste material into soluble sugars, but rather generates a product that can be more readily hydrolyzed by further processes.

Initially, the organic fraction of the waste material, which typically will include paper, consists of three primary components, cellulose, hemicellulose, and lignin. The cellulose and hemicellulose are carbohydrates made of sugars linked together in long chains called polysaccharides that form the structural portion of plant cell walls. The cellulose itself is in a crystalline structure made of glucose sugar molecules wrapped in a sheath of hemicellulose and lignin which partially protects the cellulose material from microbial attack. The initial hydrolysis of the material during the hydrothermal treatment 516 disrupts portions, or all, of the sheath, making the cellulose accessible. Further hydrolysis during the hydrothermal treatment 516 ruptures and fractions the waste material at the cellular level and leads to saccharification of the hemicellulose and cellulose fractions of the waste material, as well as partial to complete dissolution of compounds in non-cellulostic cells.

The autoclave 635 of FIG. 6 performs the hydrothermal treatment 516 in a rotating drum over approximately a two hour period. The rotating drum, typically about 8 feet in diameter and about 30 feet long, includes a door at one end for loading and unloading. The drum can be rotated up to about 10 revolutions per minutes (rpm) and can also be tilted between a negative 12 degrees for unloading to a plus 45 degrees for gravity loading. The drum operates at pressures between minus 5 pounds per square in gauge (psig) to 50 psig at temperatures from ambient to about 300° F. Suitable autoclave systems and operating conditions are described, for example, in U.S. Pat. Nos. 5,445,329 and 5,655,718.

In some embodiments, steam from the autoclave 635 is processed through an eductor 640. In the eductor 640 the steam is condensed and water-soluble volatile organic compounds that have been adsorbed by the steam can be recovered 518 (FIG. 5) for energy recovery or other uses such as producing a fertilizer product. More specifically, water is cycled from the autoclave 635 to the eductor 640 and back to the autoclave 635, and volatile organic compounds, some of which are acidic, are leached out of the waste material and concentrated in a tank of the eductor 640. The water, once saturated with volatile organic compounds, can be directed to energy recovery 510 in the anaerobic digester 620. Steam lines connecting the autoclave 635 to the eductor 640, and other supporting components for the autoclave 635 and eductor 640, such as pumps and heaters, have been omitted from FIG. 6 for clarity. Such omitted components are well known to those of ordinary skill in the art.

The partially hydrolyzed biomass from the autoclave 635 can be further screened 520, for example, with a second trommel 645 to separate out any remaining non-biomass or inert materials. A suitable screen size for the second trommel 645 is in the range of ½" to 2". It will be appreciated that the screening 520 may not be necessary where the initial waste material is sufficiently uniform and free of non-biomass or inert materials, or where the screening 508 is sufficient. Similarly, in some embodiments all of the initial waste material is sent directly to the hydrothermal treatment 516 and screening 520 is the only screening. In these embodiments, depending on the quality of the initial waste material, a sorting 522 can also be performed, for example, on a sorting line 650 like the sorting line 610 described above. As shown, recyclable items are sent for recycling 524 while inert materials are directed to landfilling 526. Alternately, as described above, the inert materials can be aerobically composted to create a soil amendment.

The unders from the screening 520, or the entire output from the hydrothermal treatment 516, in those circumstances where screening 520 is unnecessary, is directed to energy recovery 510. Energy recovery 510 can be achieved, for instance, in either a one or a two stage anaerobic digester. In some embodiments, the two stage digester 620 further hydrolyzes the partially hydrolyzed biomass, generates methane, and leaves lignin and residual material that can then be composted and biodegraded further to create a soil amendment. A suitable methanogenic process is a two stage high solids anaerobic digestion system described in U.S. Pat. No. 6,342,378. This system consists of hydrolysis and biogasification reactors that facilitate the formation of methane gas in a process that allows energy recovery in an environmentally friendly manner. Alternately, the partially hydrolyzed biomass can be processed to produce ethanol or a liquid fertilizer. In some embodiments, methane, or other products, produced by energy recovery 510 can be used to power the process 500.

The entire process 500, except the energy recovery 510 in some embodiments, takes place in a controlled environment to prevent unwanted air and water emissions. The controlled environment can be an enclosed negative air building, for example. As noted, in some embodiments any or all of the partially hydrolyzed biomass, the unders from screening 508, and the recovered volatile organic compounds, can be transported to another facility for the energy recovery 510.

Figure 7:
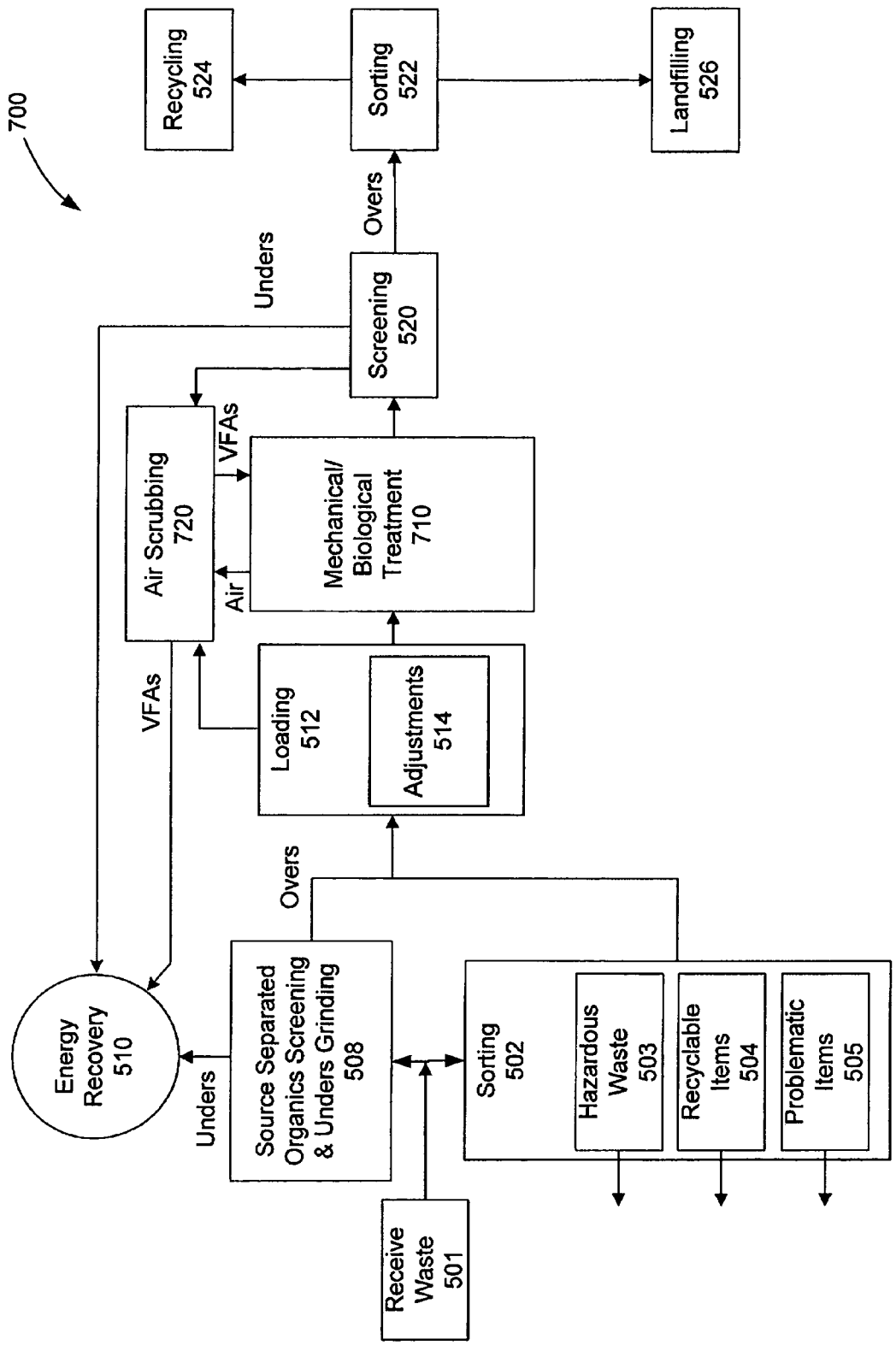
FIG. 7 is a flow diagram of a process for treating waste material in accordance with another implementation of the invention.

FIG. 7 shows still another process 700 for organic waste treatment according to an exemplary embodiment of the invention. Process 700 is similar to process 500, but provides an alternative to the hydrothermal treatment 516. This alternative includes mechanical mixing in combination with biological activity, as discussed in detail below.

In process 700, as in process 500, waste material is received 501, sorted 502, and screened 508, with unders from the screening 508 directed to energy recovery 510. Overs from the screening 508 are directed to a loading process 512. Here, the composition of the waste material can be optionally adjusted 514 as needed to obtain a more optimal mixture for further processing. For instance, drier material such as paper can be added where the moisture content of the overs is too high. Alternately, wetter materials or water can be added to the overs to increase moisture content. A suitable moisture content is about 60% but can vary between about 50% to about 65%.

Similarly, other materials can be added as needed to adjust factors such as the pH, the carbon to nitrogen ratio, and the biological content of the waste material. For instance, additional carbon or nitrogen can be added in the form of select waste or chemicals. A suitable carbon to nitrogen ratio is about 30:1, but can vary within a range of about 20:1 to about 40:1. A neutral or slightly acidic pH in the range of 5 to 6 is also preferred. The pH can be lowered, for example, by isolating and removing high pH waste or by adding select lower pH waste. Similar techniques can be employed to raise the pH. The pH can also be adjusted 514 by adding commercially available acids or bases.

The biological content of the waste material can be adjusted 514, for instance, by addition of select bacteria. The added bacteria can either be a cultured bacteria, or can be a bacteria that is recovered from a mechanical/biological treatment 710, discussed in greater detail below. In the latter case, a small fraction of a biomass produced by the mechanical/biological treatment 710 is recirculated back into the waste material. In some embodiments the small fraction of biomass added to the waste material is less than ten percent of the mass of the waste material.

The added bacteria can include any bacteria capable of facilitating a fermentation process, such as aerotolerant anaerobic bacteria. Aerotolerant anaerobic bacteria are specialized anaerobic bacteria characterized by a fermentative-type of metabolism. These bacteria live by fermentation alone, regardless of the presence of oxygen in their environment. Exemplary aerotolerant anaerobic bacteria include species in the genera *Desulfomonas, Butyrivibrio, Eubacterium, Lactobacillus, Clostridium* and *Ruminococcus*.

As in process 500, the loading process 512 in process 700 can be performed by an infeed system 630 and an optional mixer 625 for adjusting 514 the waste material. Water and/or any other adjustment materials can also be added to the waste material while in the infeed system 630. This can be done to either make additional adjustments 514 after processing in the mixer 625, or in the alternative, for adjusting 514 the composition of the waste material without using a mixer 625.

The loading process 512, in process 700, transfers the waste material to a mechanical/biological treatment 710. The mechanical/biological treatment 710 creates a partially hydrolyzed biomass through a combination of mechanical mixing and fermentation in a controlled environment. The controlled environment can be, for example, the interior of a rotating drum where the rate of mixing, temperature, oxygen content, and retention time in the drum can all be controlled. Some of these parameters can be controlled, for instance, by adjusting the rotational speed of the drum, the air flow through the drum, and the rates of feeding into, and discharge from, the drum. Additionally, the temperature, moisture content, and oxygen content of the air that is passed through the drum can also be controlled.

The environment within the mechanical/biological treatment 710 also includes aerotolerant anaerobic bacteria that facilitate a fermentation process. The fermentation partially hydrolyzes the waste material to convert, as much as possible, the biodegradable fraction thereof into volatile fatty acids and their precursors. The biomass created by the mechanical/biological treatment 710 is readily useable for fertilizer production or for energy productions such as in energy recovery process 510. Further details of the mechanical/biological treatment 710 will be discussed below with reference to FIG. 8.

The partially hydrolyzed biomass from the mechanical/biological treatment 710 can be further screened 520 to separate unders from overs, as described above with reference to process 500. The unders from the screening 520, or the entire output from the mechanical/biological treatment 710, in those circumstances where screening 520 is unnecessary, is directed to energy recovery 510. The overs from the screening 520 can be sorted 522 so that recyclable items are sent for recycling 524 and inert materials are either directed to landfilling 526 or aerobically composted to create a soil amendment.

Process 700 also includes air scrubbing 720 to recover volatile organics from the mechanical/biological treatment 710 and optionally from either or both of the loading 512 and screening 520 processes. In particular, air collected off of the processed biomass can include a high concentration of volatile fatty acids. A suitable system for air scrubbing 720 includes a water scrubbing system. Air collected from the mechanical/biological treatment 710, loading 512, and screening 520 can be scrubbed to cleanse the air and concentrate the volatile fatty acids in water. Water including volatile fatty acids from the water scrubbing system can be directed to energy recovery 510 or recycled back into the mechanical/biological treatment 710 through the adjustments 514. The cleansed air from the water scrubbing system, having a lower oxygen content, can advantageously be recycled through the mechanical/biological treatment 710. Alternatively, in an overall facility that controls odor with a negative pressure system that includes a biofilter to remove odors from the air, the cleansed air can be added to the air being directed into the biofilter.

Figure 8:
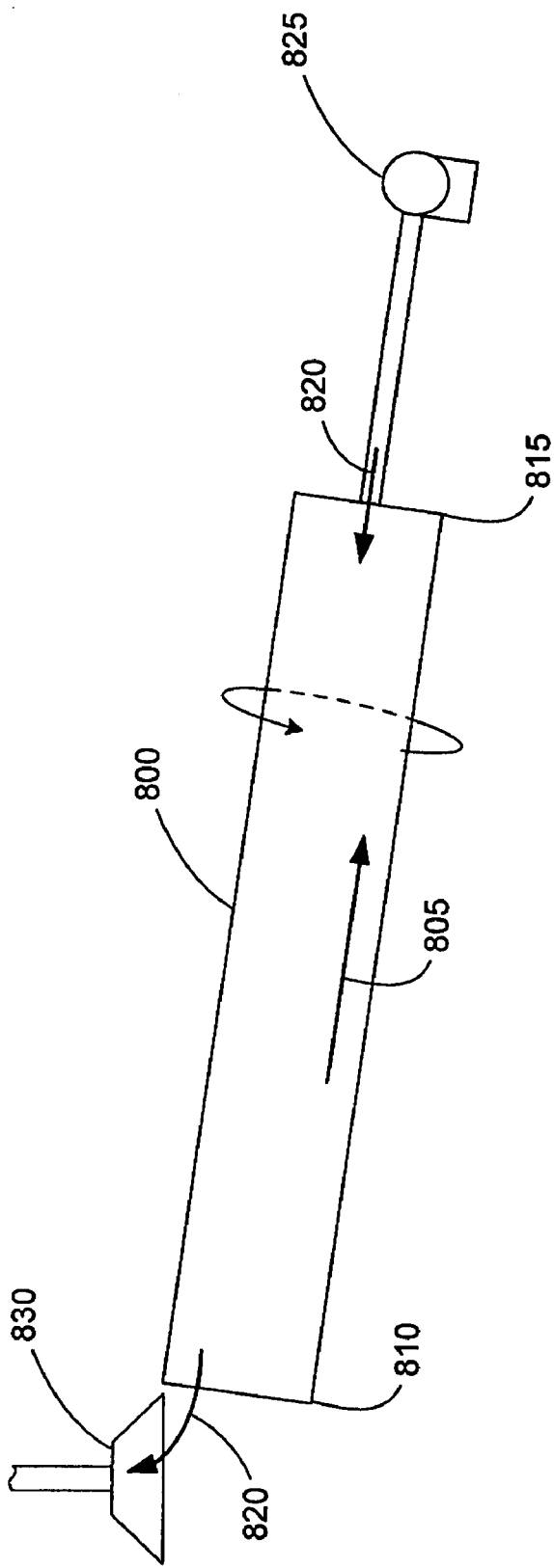
FIG. 8 depicts a biomixer in accordance with another specific implementation of the invention.

An exemplary biomixer 800 for performing the mechanical/biological treatment 710 is described with reference to FIG. 8. The biomixer 800 comprises a rotatable drum that is sloped relative to the horizontal so that waste material (represented by arrow 805) introduced at a feed end 810 traverses the biomixer 800 to a discharge end 815. Also shown in FIG. 8 is an air system for moving air (represented by arrow 820) through the biomixer 800 and for recovering the air. Specifically, the air system includes an air injector 825, such as a blower, and an air collection device 830, such as a hood.

A suitable drum for the biomixer 800 comprises a cylinder approximately 12' feet to 16 feet in diameter with a length of up to about 15 times the diameter. The drum can be sloped toward the discharge end 815 at about 3/16 of an inch per foot of length, but can be increased or decreased to adjust the rate with which waste material traverses the drum. The drum can also include access manholes, discharge ports, sampling ports, and monitoring ports. Cathodic protection can also be provided to the drum to protect the drum against excessive corrosion.

At the feed end 810 of the drum, an opening aligned with the equipment of the loading process 512, such as with an infeed system 630 (FIG. 6), prevents spillage of waste material and/or the escape of air (which can be collected through the infeed system 630 as noted below). In some embodiments the drum is loaded to about half full at the feed end 810 and thus will only have a few feet of headroom at the discharge end 815. When loaded in this way, approximately two thirds of the volume of the drum is filled by the waste material, leaving the remaining third to allow the waste material to tumble as the drum rotates. A suitable retention time is about 1.5 days, but can range from about one to about three days.

Air is discharged from the drum, for example, through a feed ram opening or through separate discharge ports in the infeed system 630. An air inlet located near the center of the discharge end 815 communicates with the air injector 825. As noted above, the air that exits the drum can be recovered and scrubbed of volatile fatty acids and optionally returned to the drum by the air injector 825.

In operation, the biodegradable fraction of the waste material, primarily paper and other organic components, is converted in the biomixer 800 to a partially hydrolyzed biomass by mechanical breakdown and fermentation. The paper fraction of the waste material becomes wet and is broken into increasingly smaller pieces by the mechanical action. Other organic components are likewise sheared by the slow rotation of the biomixer 800. At the same time, aerotolerant anaerobic bacteria in the low oxygen environment of the biomixer 800 facilitate fermentation of the biodegradable fraction. This results in the partial hydrolysis of the biodegradable fraction into volatile fatty acids and their precursors.

As noted above, the environment in the biomixer 800 is controlled to facilitate the fermentation process caused by the aerotolerant anaerobic bacteria. The environment is primarily affected by the composition of the waste material, including the choice of aerotolerant anaerobic bacteria, the rate of air flow through the environment, and the oxygen concentration of the air. In some embodiments the oxygen concentration of the discharged air (as it leaves the feed end 810) is below 3.0% and can be as low as about 0.5%. Within the biomixer 800 an oxygen level gradient can vary from about 0.5% near the feed end 810 to about 5.0% at the discharge end 815. Recycling the discharged air, after air scrubbing 720, back into the biomixer 800 helps maintain the low oxygen concentration within the biomixer 800.

As the waste material traverses the biomixer 800 towards the discharge end 815 the production of volatile fatty acids from the waste material increases, and the pH of the waste material drops to about 5.5 or lower. A pH range from the feed end 810 to the discharge end 815 can vary from about 8 to about 4.5. If necessary, the pH of the waste material can be made more basic by adjusting 514 to raise the endpoint pH within the biomixer 800 to better protect the biomixer 800 from corrosion damage, though this may reduce the efficiency of the fermentation process.

As the material traverses the biomixer 800, and the fermentation process increases, the temperature of the waste material also increases. A suitable temperature for the fermentation process is about 145° F. but the temperature can range from about 130° F. at the feed end 810 to about 165° F. at the discharge end 815. While the moisture content at the feed end 810 can be about 60%, the effect of heating of the waste material causes moisture to evaporate and be carried from the biomixer 800 with the air flow. However, even though moisture is being lost as the waste material traverses the biomixer 800, mass is also lost, for example, through the volatilization of volatile fatty acids. The overall result is that the moisture content of the waste material will range from about 60% at the feed end 810 to as low as about 40% at the discharge end 815, though a more common final moisture content is around 50%.

It will be appreciated that sensors can be implemented to measure moisture, oxygen content, pH, and temperature at different locations within the biomixer 800. The process 700 can be monitored at locations outside of the biomixer 800 as well. For instance, other sensors can measure the moisture and oxygen content and temperature of the air entering and exiting the biomixer 800, as well as the air exiting the air scrubbing 720. Based on readings from the sensors, various parameters can be varied to keep the moisture level, oxygen content, pH, and temperature in the biomixer 800 within desired ranges. These parameters can include drum rotation speed, the rates of loading and unloading, the slope of the drum relative to the horizontal, the air pressure at the discharge end 815, the moisture and oxygen content of the air being introduced into the biomixer 800, the pH and moisture content of the material being loaded into the biomixer 800, and so forth.

In the foregoing specification, the present invention is described with reference to specific embodiments thereof, but those skilled in the art will recognize that the present invention is not limited thereto. Various features and aspects of the above-described present invention may be used individually or jointly. Further, the present invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A process for treating organic waste material, comprising:
    screening the organic waste material to produce unders and overs thereof;
    treating, by fermenting and mixing, the overs of the waste material with an aerotolerant anaerobic bacteria in a controlled environment to produce a partially hydrolyzed biomass;
    passing air through the controlled environment while treating the overs therein; and
    anaerobically digesting the unders of the waste material and the partially hydrolyzed biomass.

2. The process of claim 1 wherein the waste material comprises a source separated organic waste.

3. The process of claim 1 wherein the waste material comprises municipal solid waste.

4. The process of claim 1 wherein the controlled environment includes a rotating drum.

5. The process of claim 1 further comprising sorting the waste material to remove non-organic material prior to screening the organic waste material.

6. The process of claim 1 further comprising sorting the overs after screening the waste material.

7. The process of claim 1 further comprising screening the partially hydrolyzed biomass to produce unders and overs thereof, and anaerobically digesting the unders of the partially hydrolyzed biomass.

8. The process of claim 7 further comprising sorting the overs of the partially hydrolyzed biomass.

9. The process of claim 1 further comprising adjusting a moisture content of the overs of the waste material before treating the overs in the controlled environment.

10. The process of claim 1 further comprising adjusting a pH of the overs of the waste material before treating the overs in the controlled environment.

11. The process of claim 1 further comprising adjusting a biological content of the overs, before treating the overs in the controlled environment, by adding a portion of the partially hydrolyzed biomass to the overs.

12. The process of claim 1 further comprising recovering volatile fatty acids from the air passed through the controlled environment.

13. The process of claim 12 wherein treating the overs in the controlled environment includes adding water, containing the recovered volatile fatty acids, into the controlled environment.

14. The process of claim 12 further comprising anaerobically digesting the recovered volatile fatty acids.

15. The process of claim 12 wherein recovering the volatile fatty acids includes scrubbing the air with water to cleanse the air and to concentrate the volatile fatty acids in the water.

16. The process of claim 15 wherein passing air through the controlled environment includes recycling the cleansed air into the controlled environment.

17. A process for treating organic waste material, comprising:
    screening the organic waste material to produce unders and overs thereof;
    treating, by fermenting and mixing, the overs of the waste material with an aerotolerant anaerobic bacteria in a controlled environment to produce a partially hydrolyzed biomass;
    passing air through the controlled environment while treating the overs therein; and
    recovering volatile fatty acids from the air passed through the controlled environment.

18. The process of claim 17 wherein recovering the volatile fatty acids includes scrubbing the air with water to cleanse the air and to concentrate the volatile fatty acids in the water.

19. The process of claim 18 wherein passing air through the controlled environment includes recycling the cleansed air into the controlled environment.

* * * * *